United States Patent
Zaderko et al.

(10) Patent No.: US 10,000,382 B2
(45) Date of Patent: Jun. 19, 2018

(54) METHOD FOR CARBON MATERIALS SURFACE MODIFICATION BY THE FLUOROCARBONS AND DERIVATIVES

(71) Applicants: Alexander Zaderko, Brovary (UA); Vasyl Prusov, Kyiv (UA); Vitaliy Diyuk, Kyiv (UA)

(72) Inventors: Alexander Zaderko, Brovary (UA); Vasyl Prusov, Kyiv (UA); Vitaliy Diyuk, Kyiv (UA)

( * ) Notice: Subject to any disclaimer, the term of this patent is extended or adjusted under 35 U.S.C. 154(b) by 0 days. days.

(21) Appl. No.: 15/301,954

(22) PCT Filed: Nov. 3, 2015

(86) PCT No.: PCT/UA2015/000104
§ 371 (c)(1),
(2) Date: Apr. 10, 2017

(87) PCT Pub. No.: WO2016/072959
PCT Pub. Date: May 12, 2016

(65) Prior Publication Data
US 2017/0260052 A1     Sep. 14, 2017

(30) Foreign Application Priority Data
Nov. 3, 2014   (UA) .............................. A 2014 11925

(51) Int. Cl.
| | | |
|---|---|---|
| *C07C 17/281* | (2006.01) |
| *C09C 1/56* | (2006.01) |
| *B82Y 30/00* | (2011.01) |
| *B82Y 40/00* | (2011.01) |
| *C01B 31/00* | (2006.01) |
| *C01B 31/08* | (2006.01) |
| *C01B 31/02* | (2006.01) |
| *C01B 31/04* | (2006.01) |

(52) U.S. Cl.
CPC ........ *C01B 31/005* (2013.01); *C01B 31/0253* (2013.01); *C01B 31/0484* (2013.01); *C01B 31/083* (2013.01); *C07C 17/281* (2013.01); *C09C 1/56* (2013.01); *B82Y 30/00* (2013.01); *B82Y 40/00* (2013.01); *C01B 2202/06* (2013.01); *Y10S 977/748* (2013.01); *Y10S 977/752* (2013.01); *Y10S 977/847* (2013.01)

(58) Field of Classification Search
CPC ....... C08J 7/126; C08J 2327/12; C01B 31/00; C01B 31/005; C01B 31/083
See application file for complete search history.

(56) References Cited

U.S. PATENT DOCUMENTS

| | | | | |
|---|---|---|---|---|
| 6,113,824 A | * | 9/2000 | Yamana | C08J 7/126 264/319 |
| 2010/0155221 A1 | * | 6/2010 | Powell | B01J 19/126 204/157.95 |

FOREIGN PATENT DOCUMENTS

EP         0236882 B1 *  9/1987

* cited by examiner

*Primary Examiner* — Jafar Parsa

(57) ABSTRACT

A chemical vapor deposition method for fluorine-containing carbon materials preparation provided. The claimed method comprises treating of carbons with fluorocarbons or derivatives that passes at a moderate high temperature. The fluorine-containing carbon materials show hydrophobicity, high thermal stability and can be used as catalysts support, lithium battery anodes, and hydrophobic materials or as surface precursor. Surface fluorine characterized by intensive signal in the XPS spectrum, found in a range of 685-687 eV. Obtained fluoro-containing functionalities is stable at a temperature about 1000° C.

Figure 1:
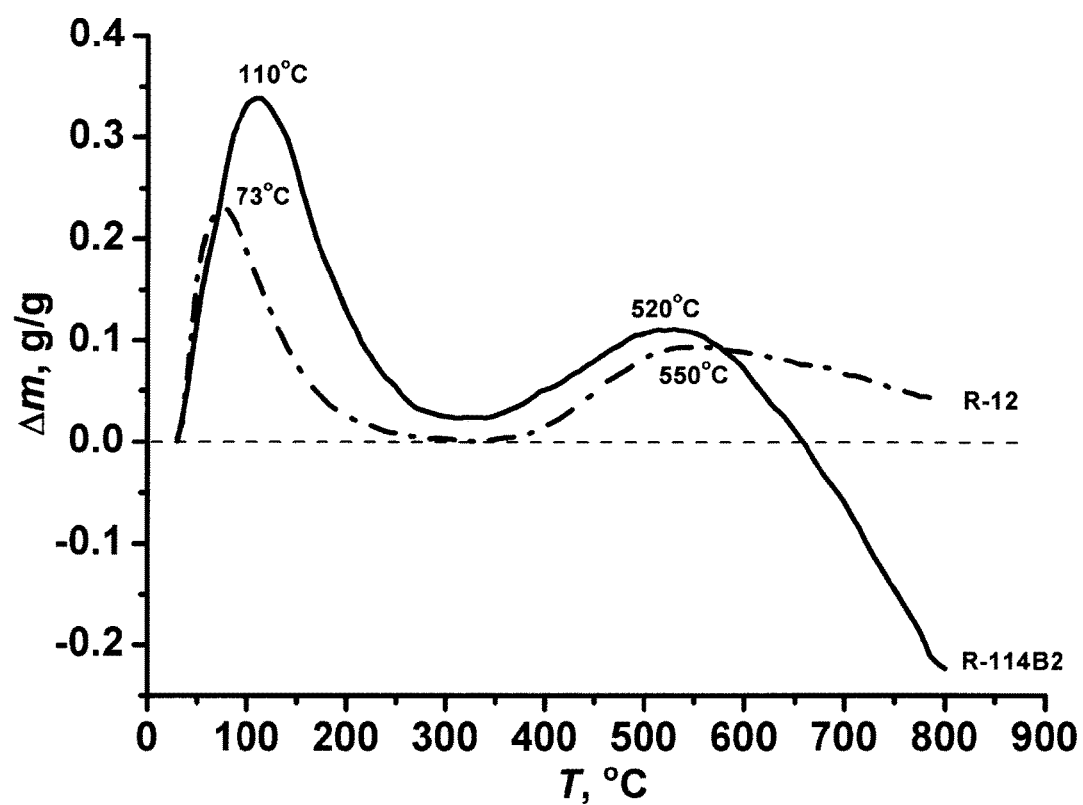

The authors propose to use Fluocar® name for materials synthesized using the claimed method.

3 Claims, 1 Drawing Sheet

METHOD FOR CARBON MATERIALS SURFACE MODIFICATION BY THE FLUOROCARBONS AND DERIVATIVES

This invention relates to method for obtaining surface-modified fluorine-containing carbon materials. Surface modification proposed is within chemical vapour deposition method for the preparation of fluorine-containing carbon materials, including porous and/or high disperse ones, by means of (per)fluoroalkylation with organic fluorine-containing compounds. This method excludes the use of fluorine gas, p, d-metals, Xe and halogen fluorides or by employing plasma deposition technique. The method can serve for the hydrophobization of the carbon materials surface and can be used for the production of sorbents, catalysts, catalyst supports, proton conductors and electrodes including that for lithium battery or fuel cells. A wide range of carbon materials with desired texture (e.g. surface area and pore volume), and chemical (e.g. chemical nature and concentration of surface functional groups) properties able to be modified by the method proposed.

Carbon materials suitable for the modification are high surface area or high dispersed ones, e.g. activated carbons, carbonizates, carbon black, thermally expanded graphite, carbon nanotubes, graphene, nanodiamonds, etc.

In turn, low-toxic Freons R-13, R-12, R-13B1, R-23, R-114, and R-11482 or industrial fluorine-containing chemicals, such as trifluoroacetic acid, trifluoroethanol, perfluoroethane and hexafluoroacetone, can serve as the fluorinating reagents.

Known from the literature methods for carbon materials modification with fluorine or fluorine-containing compounds are focused mainly on gas-phase treatment, but, as the rule, these methods operate with extremely toxic, corrosive and irritating substances, including free fluorine (for example U.S. Pat. No. 3,929,920—Process for continuous fluorination of carbon), X-ray or gamma radiation (WO2004041428 A3—Sorbent material having a covalently attached perfluorinated surface with functional groups), xenon fluoride $XeF_2$ (EP 1148945 B1—New hydrophobic polymer comprising fluorine moieties), other halogen fluorides etc., or claim the use of complex instrumentations, such as plasma generators, vacuum chambers, and other vacuum equipment.

The most common way to obtain fluorinated carbons is a low-temperature plasma obtaining of carbon materials from fluorine-containing precursor, as in U.S. Pat. No. 6,572,937—Method for producing fluorinated diamond-like carbon films.

The disadvantages of this approach are special conditions that should be used according to the method claimed. Among them are the operation pressure of 1 Pa, the use of the mixture of explosive acetylene with hexafluoroethane, necessity in a glow discharge plasma chamber, and low process productivity.

The most related to the claimed is the method of U.S. Pat. No. 7,939,141—Method of production of fluorinated carbon nanostructures by Edward Stephen Matthews, Xiaoming Duan, Richard Llewellyn Powell, where carbon materials were treated with a gaseous fluorocarbon or fluorocarbon mixture injected in a plasma camera. This one-stage method gives the fluorinated carbon materials of the general formula of $CF_x$, where x=0.06-0.15. Perfluoroethane, hexafluorobenzene, perfluoromethylcyclohexane was used as reagents. The disadvantage of this method is the notorious necessity of a special instrumentation to create plasma, a low pressure, low modification selectivity and low process productivity caused a low reagent concentration in a gas phase.

The goal of the invention is technical task to create a method of carbon materials modification using the fluorine-containing compounds under mild conditions, or at moderate temperature, i.e. excluding such factors as a very high temperature, the presence of toxic or explosive chemicals, the use of special complex fluorine-resistive equipment, carrying out reactions in the plasma, and the necessity in a vacuum instrumentation or an activation with radiation.

This task is solved by the claimed method of carbon materials modification. The method is based on chemical treatment of carbon materials with fluorine-containing compounds as fluorocarbons or perfluoroethers or derivatives, where at the least the one fluorine atom are substituted with at the least one atom, such as other halogen, hydrogen or an oxygen atom, or with thermally labile functional group, as —OH, —COH, or —COOH. If oxygen atom is chosen as the substituent, then two fluorine atoms are substituted with this atom. Moreover, substitution with oxygen atom can generate ketone, aldehyde or (cyclic) ether. Fluorocarbons is also can be used as modifier substances. Claimed method of carbon modification passes in inert medium or in a presence of water and/or oxygen, at the temperature above 200° C. The presence of water and/or oxygen supports the formation of free O,H-containing reactive species on the carbon surface that assists homolysis of fluorine-containing reagents and amplifying the yield of the grafting surface functionalities. The water and oxygen are physisorbed and chemisorbed on carbons in the most cases, so their source can be the initial carbon material.

According to the claimed method, fluorine-containing organic substance, as fluorination reagent, described within Formula, is subjected to thermal homolysis, labile group break or/and split and generates reactive species that react with active centers on the surface of the carbon material. The fluorine-containing reactive species bind chemically (covalently) and the covalent nature of this binding ensures the thermal and the hydrolytic stability of the resulted fluorinated carbon material.

Just before the contact with fluorine containing substance, the fluorination reagent, the carbon can be heated in a flow of inert gas or vacuum, to remove chemically and physisorbed water, oxygen and sorbed impurities in order to achieve lower yield of a by-product, as HF and $COF_2$.

The optimal conditions of carbon surface modification were determined from thermogravimetric experiments that are carried out typical as follows.

A quartz cup with 1 g of activated carbon, KAU, obtained from fruit stones, was treated with an argon gas, in a programmable heated tubular reactor, using the flow rate of 80 $cm^3$/min. Corresponding fluorination reagent (Freon R-12—$CF_2Cl_2$ or argon saturated with a vapor of Freon R-114B2—$BrCF_2CF_2Br$) was injected in the argon flow with the flow rate of 10 $cm^3$/min. The temperature of the reactor was linearly increased with the rate of 5° C./min. Typical temperature dependence of the mass increase is shown on FIGURE.

The effects on the thermogravimetric curve correspond to respective Freon physisorption, mass increase with maximum at 110-115° C., Freons desorption at the temperatures above 115° C. and below 300° C., and Freon chemisorption by carbon from 300° C. The reaction of Freon with the quartz cup begins at 550° C. and causes the mass loss. It was shown, by thermal programmed desorption mass spectrometry and thermogravimetric methods that fluorine-containing surface layer in inert gas medium is relatively stable at the experiment temperature, about 1000° C., and fluorine desorbs in a single form of HF at the temperature above 650° C. with low rate.

It should be noticed that, at the temperatures of the range 200-250° C., in the surface of carbon material can present reactive species, as products of the thermodestruction of surface functional groups. These species support splitting of labile atoms or groups belonging to fluorine-containing substance at a low rate.

The treatment of the carbon material, where double —CH═CH— bonds of carbon matrix act as an active center, with Freon R-12, can be illustrated by a schema

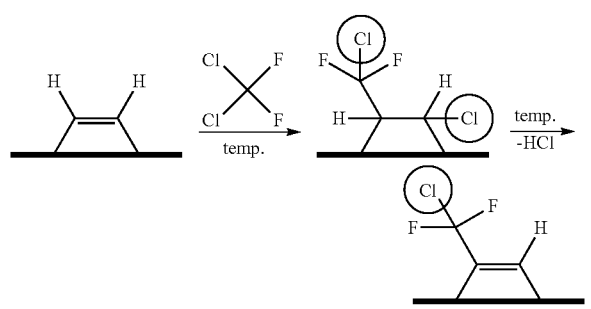

Active chlorine atoms that can be replaced with other functional groups are outlined.

Claimed method of the carbon modification allows grafting fluorine-containing (e.g. perfluoroalkyl) groups with specified structure and properties onto the surface of chosen carbon material. The some types of obtained fluorinated carbon material are precursors to sulfur- or nitrogen-containing surface species that could be used for preparation of carbons with high thermal stability and hydrophobicity, which can serve as selective sorbents, catalysts, metal catalyst support and battery electrodes.

EXAMPLES

Example 1

5 g of carbon material as activated carbon, of trade mark SCN, obtained from carbonized sulphonated polyvinyl-pyridine resin, was heated in purged Ar gas at the flow rate of 50 ml/min to 450° C. and stored at the temperature of 550° C. for 2 h. This stage is necessary for water, CO, $CO_2$ and physisorbed molecules desorption. Fluorinating reagent such as a Freon gas R-12, $CF_2Cl_2$, was mixed to an argon flow to treat the activated carbon surface. The treatment was performed at the flow rate of Freon gas of 35 ml/min at the treatment temperature of 550° C. during 2 h. After the treatment, the resulting modified activated carbon was cooled in the Ar flow to r.t. Chemical analysis proves that obtained activated carbon contains 2.07 mmol/g of chlorine and 1.96 mmol/g of fluorine. XPS spectrum shows F and Cl peaks for the fluorinated activated carbon. Peak of F 1s is symmetric with the maximum at 686.8 eV. The Cl 2p doublet components are observed at 199.5 eV (Cl $2p_{3/2}$) and 201 eV (Cl $2p_{1/2}$). Energies of fluorine and chlorine binding refer to that of $CF_2$-groups in organic fluorides and Cl-groups in organic chlorides.

Example 2

The process of Example 1 is carried out, but, with activated carbon, KAU, obtained from carbonized fruit stones and as fluorinating reagent was used Ar gas saturated with vapors of R-114B2, $BrF_2C$—$CF_2Br$, the saturation was done at the temperature of 0° C. Obtained fluorinated carbon contains 0.85 mmol/g of bromine and 3.98 mmol/g of fluorine.

Example 3

5 g of multiwalled carbon nanotubes, which is obtained by CVD method from methane over Ni catalyst, BET surface of 115 $m^2/g$ and pore volume of 0.12 $cm^3/g$, was treated as in Example 1, but with Freon R-114 ($ClCF_2CF_2Cl$) as fluorinating agent. Obtained fluorinated carbon contains 0.42 mmol/g of chlorine and 0.90 mmol/g of fluorine.

Example 4

5 g of carbon black of K-354 of native trademark was treated as in Example 1, but with Freon R-13 ($CClF_3$) and the treatment was carried out at the temperature of 570° C. Obtained fluorinated carbon contains 0.72 mmol/g of chlorine and 2.30 mmol/g of fluorine.

Example 5

5 g of activated carbon of native SCN trademark was as in Example 2, but with trifluoroacetic acid ($CF_3COOH$) as fluorinating reagent and the treatment was carried out at the temperature of 480° C. Obtained fluorinated carbon contains 2.55 mmol/g of fluorine.

Example 6

The process of Example 1 is carried out, but, with 1 g of graphene (BET surface of 480 $m^2/g$) synthesized by pyrolysis of sodium ethylate as carbon material. Obtained fluorinated carbon contains 0.52 mmol/g of fluorine and 0.49 mmol/g of chlorine.

Example 7

The process of Example 1 is carried out, but, with Halone 134a, Forane®, $CH_2FCF_3$, as fluorinating reagent at the temperature of 575° C., and 50 ppm of oxygen was added to a flow of the fluorinating reagent. Obtained fluorinated carbon contains 2.94 mmol/g of fluorine. Intensive XPS F 1s signal with two component maximums at 685.5 eV and 686.4 eV is registered for this fluorinated carbon. These components refer to two different surface fluorine forms, one of which corresponds to $CF_3$-groups. 0.5 g of the obtained fluorinated carbon was heated in purged argon gas flow at 1000° C. for 2 h. The resulted fluorine-containing carbon contains 2.05 mmol/g of residual fluorine. That confirms high thermal stability of fluorine-containing surface layer obtained.

Example 8

The process of Example 7 is carried out, but, with no oxygen addition to a fluorinating agent. Resulting fluorinated carbon contains 1.75 mmol/g of fluorine.

Example 9

The process of Example 7 is carried out, but, without oxygen gas in a fluorinating agent flow. Instead oxygen, an admixture of water was added to Forane™, $CH_2FCF_3$, flow by the gas bubbling through the water at 0° C. Resulting fluorinated carbon contains 3.92 mmol/g of fluorine.

Example 10

The process of Example 1 is carried out, but, with 5 g of activated carbon, KAU, as carbon material and with hexafluoroacetone, $CF_3COCF_3$, as fluorinating reagent. Obtained fluorinated carbon contains 0.32 mmol/g of fluorine.

Example 11

The process of Example 1 is carried out, but, with hexafluoroacetone instead of Freon R-12. Obtained fluorinated carbon contains 0.60 mmol/g of fluorine. XPS spectrum shows F1s symmetric peak centered at 685.3 eV that confirms the fluorination.

Example 12

3 g of activated carbon Norit® GAC 830EN, which preliminary de-ashed with diluted HCl solution, was treated as in the Example 2, but, with 2,3,5,6-tetrafluorobenzaldehyde (97%, Sigma-Aldrich) vapor as the fluorinating reagent at the temperature of 620° C. Obtained fluorinated carbon contains 0.81 mmol/g of fluorine.

Example 13

3 g of activated carbon Norit® GAC 830EN de-ashed with diluted HCl solution was treated as in the Example 2, but the treatment was carried out at the temperature of 200° C. during 9 h. Obtained fluorinated carbon contains 0.13 mmol/g of fluorine.

Example 14

1 g of activated carbon SCN was treated with an isoflurane, $C_3H_2ClF_5O$, 1-chloro-2,2,2-trifluoroethyl difluoromethyl ether, Aldrich$^{CPR}$, as in Example 2, but the treatment was carried out at 570° C. and it accompanies with intense HF and HCl evaluation. Obtained fluorinated carbon contains 3.65 mmol/g of fluorine and 0.52 mmol/g of chlorine.

Given examples clarify the invention but do not limit the scope of the rights arising from it.

What is claimed is:

1. A process for preparing of fluorinated carbon materials through chemical modification of starting porous carbon materials, selected from the group consisting of activated carbon, coke, pitch coke, charcoal, carbon fibers from synthetic or natural row, carbon nanotubes, carbon black, graphene and carbonizates, by gas phase treatment of said carbon materials in inert medium with gas or vapor of organofluorine compounds at a temperature above 200° C., at which the surface of said porous carbon materials processed with said organofluorine compounds, namely fluorocarbon derivatives that contains at least one of the following substituent selected from the group consisting of —H, -Hal, —OH, —COH, —COOH and =O, wherein the chemical reaction between said carbon materials and said organofluorine compounds is activated by thermal heating of the said carbon material, while in contact with said organofluorine compound in inert medium.

2. The process for preparing of fluorinated carbon materials as claimed in claim 1, wherein starting carbon material is subjected to the preliminary heating in an inert gas medium or a vacuum at a temperature above 200° C.

3. The process for preparing of fluorinated carbon materials as claimed in claim 1, wherein oxygen and/or water is present in the reaction gas mixture.

\* \* \* \* \*